United States Patent [19]

Audeh

[11] Patent Number: 5,393,505
[45] Date of Patent: Feb. 28, 1995

[54] PROCESS FOR INCREASING THE ACID GAS ABSORPTION CAPACITY OF CONTAMINATED ALKANOLAMINE SOLUTIONS

[75] Inventor: Costandi A. Audeh, Princeton, N.J.

[73] Assignee: Mobil Oil Corporation, Fairfax, Va.

[21] Appl. No.: 95,569

[22] Filed: Jul. 19, 1993

Related U.S. Application Data

[60] Continuation-in-part of Ser. No. 856,265, Mar. 23, 1992, abandoned, which is a continuation-in-part of Ser. No. 802,586, Dec. 5, 1991, Pat. No. 5,292,493, which is a continuation-in-part of Ser. No. 628,310, Dec. 17, 1990, abandoned, which is a continuation-in-part of Ser. No. 542,282, Jun. 22, 1990, abandoned, which is a continuation of Ser. No. 288,392, Dec. 22, 1988, abandoned, which is a division of Ser. No. 113,316, Oct. 28, 1987, Pat. No. 4,795,565.

[51] Int. Cl.$^6$ ............... C01B 17/16; C08J 5/20
[52] U.S. Cl. ........................ 423/228; 521/26; 423/229
[58] Field of Search .................. 521/26; 423/228, 229

[56] References Cited

U.S. PATENT DOCUMENTS

| Re. 29,428 | 10/1977 | Homberg et al. | 423/228 |
|---|---|---|---|
| 2,161,663 | 6/1939 | Baehr et al. | 423/229 |
| 2,797,188 | 6/1959 | Taylor, Jr. et al. | 423/229 |
| 3,658,462 | 4/1972 | Van Leroy | 423/229 |
| 5,006,258 | 4/1991 | Veatch et al. | 210/681 |

*Primary Examiner*—G. S. Kishore
*Assistant Examiner*—Peter F. Kulkosky
*Attorney, Agent, or Firm*—Alexander J. McKillop; Dennis P. Santini; Robert B. Furr, Jr.

[57] ABSTRACT

The present invention includes a process for rejuvenating a spent aqueous alkanolamine solution comprising use of alkyl-substituted ammonium-containing organic base treatment to remove inorganic ions.

14 Claims, 1 Drawing Sheet

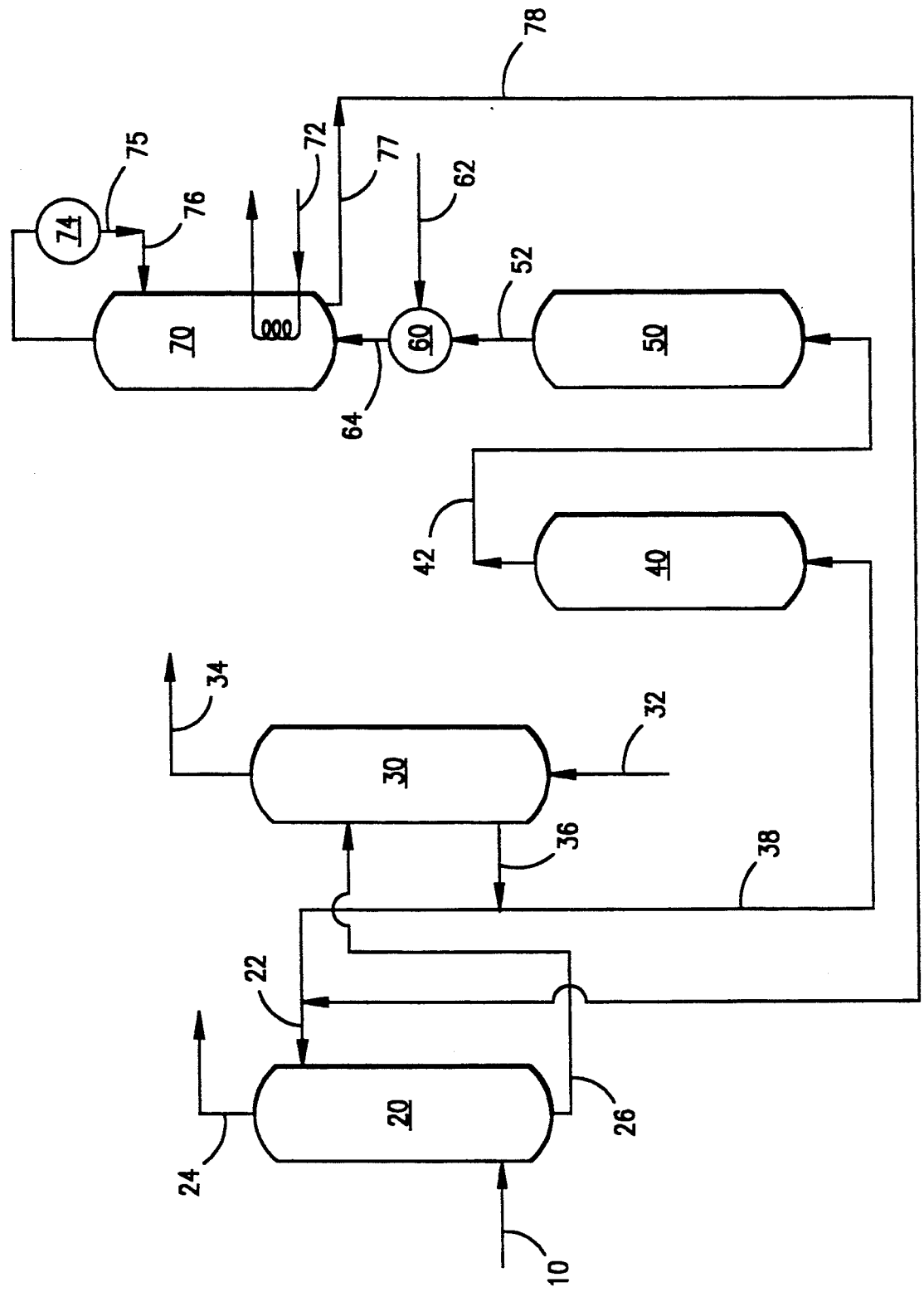

PROCESS FOR INCREASING THE ACID GAS ABSORPTION CAPACITY OF CONTAMINATED ALKANOLAMINE SOLUTIONS

CROSS-REFERENCE TO RELATED APPLICATIONS

This is a continuation-in-part of U.S. application Ser. No. 07/856,265, filed Mar. 23, 1992, and now abandoned, which is a continuation-in-part of U.S. application Ser. No. 07/802,586, filed Dec. 5, 1991, now U.S. Pat. No. 5,292,493, which is a continuation-in-part of U.S. application Ser. No. 07/628,310, filed Dec. 17, 1990, now abandoned, which is a continuation-in-part of U.S. application Ser. No. 542,282, filed Jun. 22, 1990, and now abandoned, which is a continuation of U.S. application Ser. No. 288,392, filed Dec. 22, 1988, now abandoned, which is a division of U.S. application Ser. No. 113,316, filed Oct. 28, 1987, now U.S. Pat. No. 4,795,565. The disclosures of these U.S. Applications are incorporated herein by reference.

FIELD OF THE INVENTION

The present invention relates generally to the field of gas purification. More specifically, the invention relates to the use of ethanolamine sorbents in hydrocarbon gas deacidification.

BACKGROUND OF THE INVENTION

Alkanolamine process units remove $H_2S$ and $CO_2$ from gaseous process streams, typically by countercurrently contacting an aqueous solution containing from about 20% to about 50% by weight of an alkanolamine with a gas stream containing $H_2S$ and/or $CO_2$. For the purpose of this application, it is understood that the terms "alkanolamine" and "ethanolamine" are generic terms including, but not limited to, monoethanolamine, diethanolamine, triethanolamine, and methyl diethanolamine.

The removal of hydrogen sulfide from gaseous streams, such as the waste gases liberated in the course of various chemical and industrial processes, for example, in wood pulping, natural gas and crude oil production and in petroleum refining, has become increasingly important in combating atmospheric pollution. Hydrogen sulfide containing gases not only have an offensive odor, but such gases may cause damage to vegetation, painted surfaces and wildlife, and further may constitute a significant health hazard to humans. Government-wide regulations have increasingly imposed lower tolerances on the content of hydrogen sulfide which can be vented to the atmosphere, and it is now imperative in many localities to remove virtually all the hydrogen sulfide under the penalty of an absolute ban on continuing operation of a plant or the like which produces the hydrogen sulfide-containing gaseous stream. Solutions of water and one or more the alkanolamines are widely used in industry to remove hydrogen sulfide and carbon dioxide from such gaseous streams.

Corrosion in alkanolamine units significantly increases both operating and maintenance costs. The mechanisms of corrosive attack include general corrosive thinning, corrosion-erosion, and stress-corrosion cracking. Corrosion control techniques include the use of more expensive corrosion and erosion resistant alloys, continuous or periodic removal of corrosion-promoting agents in suspended solids by filtration, activated carbon adsorption, or by the addition of corrosion inhibitors. (See Kohl, A. L. and Reisenfeld, F. C., *Gas Purification*, Gulf Publishing Company, Houston, 1979, pp. 91-105, as well as K. F. Butwell, D. J. Kubec and P. W. Sigmund, "Alkanolamine Treating", *Hydrocarbon Processing*, March, 1982.)

Further, it has been found that the acid gas sorption capacity in a circulating alkanolamine-water system decreases with time on stream in the absence of added makeup alkanolamine. This performance degradation has been found to be partially attributable to the accumulation of heat stable salts. U.S. Pat. No. 4,795,565 to Yan describes a process for removing heat stable salts from an ethanolamine system by the use of ion exchange resins. The disclosure of U.S. Pat. No. 4,795,565 to Yan is incorporated herein by reference for the operating details both of an ethanolamine acid gas sorption system as well as for the heat stable salt removal process. See also Keller et al., *Heat Stable Salt Removal From Amines by the HSSX Process Using Ion Exchange*, presented to The Laurence Reid Gas Conditioning Conference, Mar. 2, 1992.

The chemistry of alkanolamine degradation is discussed in the Butwell et al. article cited above. Briefly, the Butwell et al. article notes that monoethanolamine (MEA) irreversibly degrades to N-(2-hydroxyethyl) ethylene diamine (HEED). HEED shows reduced acid gas removal properties and becomes corrosive at concentrations of at least about 0.4% by weight.

Diglycolamine (DGA), on the other hand, is said to produce a degradation product upon reaction with $CO_2$ which exhibits different properties. DGA, a registered trademark of Texaco, Inc., identifies an amine having the chemical formula $NH_2—C_2H_4—O—C_2H_4—OH$. DGA degrades in the presence of $CO_2$ to form N,N'-bis(hydroxyethoxyethyl) urea (BHEEU) which is similar to HEED in corrosivity but differs in that BHEEU has no acid gas removal properties.

Diethanolamine (DEA) reacts with $CO_2$ to form N,N'-di(2-hydroxyethyl) piperazine. Unlike HEED and BHEEU, the piperazine compound is noncorrosive and has acid gas removal properties essentially equal to its parent, DEA. See the Butwell et al. article at page 113.

Diisopropylamine (DIPA) readily degrades in the contact with $CO_2$ to form 3-(2-hydroxypropyl) 5-methyl oxazolidone which shows essentially no acid gas removal properties. See the Butwell et al. article at page 113.

SUMMARY OF THE INVENTION

The present invention provides a process for rejuvenating a spent aqueous alkanolamine solution comprising the steps of:
  (a) providing a fresh aqueous alkanolamine solution having alkanolamine concentration sufficient to effectively sorb an acid gas selected from the group consisting of $H_2S$, $CO_2$, or both from a gaseous hydrocarbon stream having $H_2S$, $CO_2$, or both dissolved therein;
  (b) contacting said fresh aqueous alkanolamine solution with said hydrocarbon gas stream of step (a) whereby said fresh aqueous alkanolamine solution is enriched in said acid gas sorbed from said gaseous hydrocarbon stream;
  (c) stripping said acid gas from said enriched alkanolamine solution to produce an acid-lean alkanolamine solution;

(d) recycling said acid-lean alkanolamine solution of step (c) to said contacting step (b);

(e) sequentially repeating steps (b), (c), and (d) to evolve a spent alkanolamine solution which, in its acid-lean form, is characterized by reduced acid gas sorption capacity in comparison with said fresh aqueous alkanolamine solution;

(f) removing inorganic ions from said spent alkanolamine solution;

(g) heating said spent alkanolamine solution of step (f) at temperature of from about 220° to about 275° C. for time of from about 0.25 to about 2 hours in the absence of added catalyst;

(h) admixing said heat-treated spent alkanolamine solution of step (g) with at least one organic base which evolves no inorganic ionic constituent upon dissolution in said spent alkanolamine solution and heating said admixture to reflux for time sufficient to produce a rejuvenated alkanolamine solution having at least about 80% of the acid gas sorption capacity of said fresh alkanolamine solution whereby the content of inorganic ionic constituent in said rejuvenated alkanolamine solution is less than with a base which forms an inorganic ionic constituent;

(i) charging said rejuvenated alkanolamine solution to said recycling step (d).

The organic base useful in the present invention does not increase the heat stable salt accumulation in the treated solution; in comparison, the same process steps using an inorganic base such as NaOH or KOH which increase the heat stable salt accumulation by a factor of at least about 80.

The initial thermal treatment step is typically from about five (5) minutes to about three (3) hours, preferably from about fifteen (15) minutes to about two (2) hours, at temperatures within the range of from about 220° to about 275° C., more preferably from about 240° to about 260° C., in the absence of added catalyst. The subsequent organic base treatment step comprises admixing the alkanolamine solution with a suitable organic base in concentration of from about 0.1 to about 20 weight percent, preferably from about 0.5 to about 15 weight percent, more preferably from about 1.0 to about 2.0 weight percent of the total aqueous alkanolamine solution. These combined treatment steps typically improve the acid gas sorption capacity of the aqueous alkanolamine solution by a factor of from about 1.10 to about 1.30. Treating the aqueous alkanolamine solution under the preferred conditions generally improves the acid gas sorption capacity of the aqueous alkanolamine solution by a factor of from about 1.20 to about 1.30.

BRIEF DESCRIPTION OF THE DRAWING

The FIGURE is a simplified schematic diagram illustrating the major processing steps of one embodiment of the present invention.

DETAILED DESCRIPTION

The essential steps of the invention include (i) ion removal, (ii) reaction at elevated temperature in the absence of added catalyst, and (iii) reaction with organic base at elevated temperature. The fraction of lean alkanolamine which should be treated varies with the extent of contamination. It can range between 0 and 100%, but 4–20% is preferred. It should be pointed out that this clean up loop should be operated continuously to ensure smooth operation. However, it can be operated intermittently. For example, the clean up loop can be shut down during the regeneration of the anionic or cationic resins and/or during filter change over.

The Ion Removal Step

The first step in the process of the invention is ion removal. This step may be carried out by any suitable means, however, it is preferred to treat the alkanolamine solution with ion exchange resins. Following the ion removal step, the alkanolamine solution typically contains not more than about 100 ppm inorganic anions, not more than about 400 ppm organic anions, and not more than about 150 ppm inorganic cations. The ion concentrations in the alkanolamine solution after the ion removal step are preferably as low as possible.

While it is preferred for the anionic resins to precede the cationic resins in the cleanup loop, it should be understood that the reverse order will also achieve the desired result. Because regenerants such as $NH_4HCO_3$, $NH_4OH$ and $(NH_4)CO_3$ are used with the weak ion exchange resins in the present invention, the resins may be contained in separate vessels or optionally in separate beds in a single vessel.

The Anionic Exchange Resin

The weak anionic exchange resins useful in the present invention are characterized by pKa values of from about 7 to about 14 preferably from about 8 to about 12. These weak anionic exchange resins may be further characterized by their matrix structures, which include polystyrenes, epoxy-amines, phenolics, and condensates. Examples of suitable weak anionic exchange resins include those identified by the following tradenames: Allassion A33-03, Amberlite IRA-45, Amberlite IRA-93, De-Acidite G, De-Acidite M, Dowex 3, Imac A-20, Imac A-21, Ionac A-315, Lewatit MP-60, Allassion AWB-3, Anionite EDE-10P, Anionite AV-16, Dowex 44, Duolite A-30B, Duolite A-57, Imac, Ionac A-300, Ionac A-310, Wofatit L-150, Anionite AN-2F, De-Acidite E, Duolite A-6, Duolite A-7, Lewatit MIH 59 and Wofatit MD. For a survey of the chemistry of these useful weak ion exchange resins, see Irving L. Abrams and L. Benezra "Ion Exchange Polymers" 7 *Encyclopedia of Polymer Science and Technology* 706, (1967).

The Cationic Exchange Resin

The weak cationic exchange resins useful in the present invention are characterized by pKa values of from about 1 to about 7, preferably from about 2 to about 6. Most of the cationic exchange resins useful in the invention contain carboxylic acid groups, although weak cationic resins containing phenolic acid derivatives are also useful. For a survey of the chemistry of suitable weak cation exchange resins, see Irving L. Abrams and L. Benezra "Ion Exchange Polymers" 7 *Encyclopedia of Polmer Science and Technology* 704, (1967). Examples of suitable weak cationic exchange resins include those identified by the following tradenames: Allassion CC, Amberlite IRC-50, Amberlite IRC-84, Dowex CCR-1, Duolite ES-63, Duolite ES-80, Duolite CS-100, Duolite CS-101, Imac Z-5, Ionac C-270, Kastel C-100, Lewatit CNO, Wofatif CP-300, Wofatit CN, Zeo-Karb 216, and Zeo-Karb 226.

In a preferred embodiment, the anionic exchange resin is followed by the cationic exchange resin. The exchange resins may be contained in separate vessels or in a single mixed bed vessel. While it is preferred to arrange the exchange resins in series with the cationic exchange resin following the anionic exchange resin, the resins may also be placed in series with the anionic exchange resin following the cationic exchange resin.

The mixed bed in a single vessel is made up of two zones, in series, each containing a different type of ion exchange resin, for example, anionic exchange resin followed by cationic exchange resin.

Initial Reaction at Elevated Temperature

The initial heating step is suitably carried out at temperatures within the range of from about 220° to about 275° C., more preferably from about 240° to about 260° C., and is conducted in the absence of added catalyst.

The Reaction with Strong Organic Base

Following the initial heating at elevated temperature, the aqueous alkanolamine solution is admixed with a suitable organic base in concentration of from about 0.1 to about 20 weight percent, preferably from about 0.5 to about 15 weight percent, more preferably from about 1.0 to about 2.0 weight percent of the total aqueous alkanolamine solution. The base must be organic, and must form no inorganic ionic constituent upon dissolution in the aqueous alkanolamine solution. This characteristic of the strong organic base is critical; substitution of a strong inorganic base, or a base which evolves an inorganic constituent upon dissolution in the cyclic alkanolamine system of the invention markedly deteriorates the acid gas sorption capacity of the alkanolamine solution, thus defeating the purpose of the present invention.

The Strong Organic Base

Suitable strong organic bases useful in the present invention are characterized by good solubility in an aqueous alkanolamine solution. Strong organic bases useful in the present invention form no inorganic ionic constituent upon dissolution in the aqueous alkanolamine solution of the invention, and, surprisingly, appear to cause no deterioration in acid gas sorption capacity when the rejuvenated base-containing alkanolamine solution is recycled for acid gas sorption service in a substantially closed cyclic system. In contrast, the addition of strong inorganic base (e.g., NaOH) to the alkanolamine solution has been found to markedly deteriorate the acid gas sorption capacity of the alkanolamine solution, and defeats the purpose of the present process.

Examples of strong organic bases useful in the present invention include the tetraalkylammonium hydroxides, such as tetramethylammonium hydroxide, tetraethylammonium hydroxide, tetrapropylammonium hydroxide, and tetrabutylammonium hydroxide, merely to name a few. Of these strong organic bases, tetrabutylammonium hydroxide is particularly preferred.

Process Flow

Referring to the FIGURE, the crude gas 10 containing $CO_2$ and/or $H_2S$ is passed upwardly through the ethanolamine absorber column 20, where the crude gas is countercurrently contacted with lean ethanolamine solution 22. The lean ethanolamine solution 22 absorbs the $CO_2$ and $H_2S$, thereby purifying the gas. The purified gas stream 24 exits the top of the ethanolamine absorber column 20. Upon absorption of $CO_2$ and $H_2S$, the lean ethanolamine solution 22 becomes a rich ethanolamine solution 26.

The rich ethanolamine 26 is charged to the top of a stripper tower 30 and is stripped with steam 32 at about 240° F. to remove the $CO_2$ and $H_2S$ as an overhead stream 34. Upon stripping, the rich ethanolamine 26 becomes the total lean ethanolamine stream 36. The total lean ethanolamine stream 36 exits the bottom of the steam stripper tower 30 and is returned to the absorber 20 to start another cycle of absorption/stripping. However, a fraction of the total lean ethanolamine stream 36 is split off as stream 38 for regeneration. Stream 38 may optionally be filtered, for example, as is taught in U.S. Pat. No. 4,795,565 to Yan. Stream 38 is then fed to an ion exchange unit 40 which preferably comprises at least one anionic exchange resin to remove anionic species, such as $SO_4^=$, and $Cl^-$, together with at least one cationic exchange resin to remove cations such as $Na^+$, $K^+$, and $C^{++}$. The cleaned lean ethanolamine solution 42 is then charged to reactor 50 where the lean alkanolamine is heated to a temperature of about 260° C. and held at temperature for about ¾ hour. The reactor effluent 52 is the charged to a static mixer 60 to which is also added a stream containing an organic base 62. The mixed charge stream 64 is then heated to reflux at about 120°–140° C. in vessel 70 which is equipped with steam coils 72 and overhead condenser 74. A portion of the overhead condensate 75 is returned to the top of vessel 70 through line 76. The rejuvenated alkanolamine is recycled to the absorber 20 as stream 78. No organic base removal step is required to recycle stream 78 directly to absorber 20. With the exception of minor equipment leakage or evaporative losses, the present process permits the alkanolamine sorption system to operate as a substantially closed alkanolamine loop with no substantial fresh makeup alkanolamine required.

EXAMPLE NO. 1

A spent aqueous diethanolamine solution containing both inorganic and organic anions was treated in three steps in accordance with the invention. The three steps comprise (i) ion removal, (ii) reaction at elevated temperature, and (iii) treatment with organic base at elevated temperature. In the first step, the solution was treated to reduce the concentration of these anions to about 100 ppm inorganic and about 400 ppm organic, respectively. The solution was also treated to reduce the level of inorganic cations to about 140 ppm. The solution was then heated to about 260° C. and held at temperature for about ¾ hour. The solution was then admixed with about 2% by weight of the strong organic base tetramethylammonium hydroxide pentahydrate and heated to reflux at about 120° C. After about two hours at relux, the mixture was cooled and its $H_2S$ sorption capacity was tested.

| Solution | $H_2S$ Absorption Capacity, mols $H_2S$ per 100 grams of solution |
|---|---|
| Spent aqueous DEA solution before treatment | 0.26 |
| Aqueous DEA solution after ion removal and elevated temperature reaction (Step (i) and (ii)) | 0.37 |
| Aqueous DEA solution after ion removal, elevated temperature reaction, and treatment with organic base | 0.46 |

| Solution | H₂S Absorption Capacity, mols H$_2$S per 100 grams of solution |
|---|---|
| at elevated temperature. | |

Thus the present process restores acid gas sorption capacity to a spent alkanolamine solution while requiring no organic base removal step after treatment. The rejuvenated alkanolamine solution may be recycled directly to an alkanolamine acid gas sorption tower, thus permitting acid gas sorption with a substantially closed circulating alkanolamine system, and eliminating the expense associated with continuous addition of fresh makeup alkanolamine.

EXAMPLE NO. 2

The procedure of Example No. 1 was repeated but the temperature was held at room temperature. The H$_2$S sorption capacity was 0.30 mols per 100 grams of solution.

EXAMPLE NO. 3

The procedure of Example No. 1 was repeated but the temperature was held at 180° C. The H$_2$S sorption capacity after this thermal treatment step was 0.31 moles per 100 grams of solution.

EXAMPLE NO. 4

The procedure of Example No. 1 was repeated but the temperature was held at 210° C. The H$_2$S sorption capacity after this thermal treatment step was 0.31 moles per 100 grams of solution.

RESULTS OF EXAMPLES 1–4

The results of Examples 1–4 show that heating the solution to below 220° C. does not increase the H$_2$S sorption capacity of the DEA solution which had been treated for the removal of ions.

EXAMPLE NO. 5

The procedure of Example No. 1 was repeated but in place of the organic base (2% by weight), NaOH was added to the solution and the solution was refluxed as described in Example No. 1. The resultant solution showed an increase in the sodium ion concentration from about 150 parts per million to about 12,000 parts per million. This is an approximately 80 fold increase in the inorganic ion concentration. This increase in the inorganic ion concentration is an undesirable result and requires a repeat of the ion exchange step described for removing inorganic ions from the DEA solution. The H$_2$S sorption capacity of the solution was 0.44 moles per 100 grams of solution. The results of Example No. 5 show that treatment with an inorganic base produces an undesirable increase in the concentration of inorganic ions and would require re-treatment of the DEA solution to remove these inorganic ions introduced by the inorganic base.

Changes and modifications in the specifically described embodiments can be carried out without departing from the scope of the invention which is intended to be limited only by the scope of the appended claims.

What is claimed is:

1. A process for rejuvenating a spent aqueous alkanolamine solution comprising the steps of:
   (a) providing a fresh aqueous alkanolamine solution having alkanolamine concentration sufficient to effectively sorb an acid gas selected from the group consisting of H$_2$S, CO$_2$, or both from a gaseous hydrocarbon stream having H$_2$S, CO$_2$, or both dissolved therein;
   (b) contacting said fresh aqueous alkanolamine solution with said hydrocarbon gas stream of step (a) whereby said fresh aqueous alkanolamine solution is enriched in said acid gas sorbed from said gaseous hydrocarbon stream;
   (c) stripping said acid gas from said enriched alkanolamine solution to produce an acid-lean alkanolamine solution;
   (d) recycling said acid-lean alkanolamine solution of step (c) to said contacting step (b);
   (e) sequentially repeating steps (b), (c), and (d) to evolve a spent alkanolamine solution which, in its acid-lean form, is characterized by reduced acid gas sorption capacity in comparison with said fresh aqueous alkanolamine solution;
   (f) removing inorganic ions from said spent alkanolamine solution;
   (g) heating said spent alkanolamine solution of step (f) at temperature of from about 220° to about 275° C. for time of from about 0.25 to about 2 hours in the absence of added catalyst;
   (h) admixing said heat-treated spent alkanolamine solution of step (g) with an aqueous solution containing from about 0.1 to about 20 weight percent of at least one alkyl-substituted ammonium-containing organic base which evolves no inorganic ionic constitutent upon dissolution in said spent alkanolamine solution and heating said admixture to reflux for time sufficient to produce a rejuvenated alkanolamine solution having at least about 80% of the acid gas sorption capacity of said fresh alkanolamine solution whereby the content of inorganic ionic constituent in said rejuvenated alkanolamine solution is less than when the same process is carried out with a base which forms an inorganic ionic constituent;
   (i) charging said rejuvenated alkanolamine solution to said recycling step (d).

2. The process of claim 1 wherein said inorganic ion removal step (g) produces an alkanolamine solution containing not more than about 100 ppm inorganic anions and not more than about 150 ppm inorganic cations.

3. The process of claim 1 wherein said organic base is at least one selected from the group consisting of tetramethylammonium hydroxide, tetraethylammonium hydroxide, tetrapropylammonium hydroxide, and tetrabutylammonium hydroxide.

4. The process of claim 3 wherein said organic base comprises tetrabutylammonium hydroxide.

5. The process of claim 3 wherein said refluxing of step (h) is conducted at temperature of from about 120° to about 140° C.

6. The process of claim 1 wherein said rejuvenated alkanolamine solution of step (h) is charged to said recycling step (d) in the absence of an organic base removal step.

7. The process of claim 1 wherein step (g) further comprises reacting said aqueous alkanolamine solution at temperature of from about 240° to about 260° C., and step (h) further comprises admixing the alkanolamine solution with said organic base in concentration of from about 0.1 to about 20 weight percent improve the acid gas sorption capacity of the aqueous alkanolamine solution by a factor of from about 1.10 to about 1.30, whereby the content of inorganic ionic constituent in said rejuvenated alkanolamine solution is not increased and is less than with a base which forms an inorganic ionic constituent by a factor of at least about 80.

8. A process for rejuvenating a spent aqueous alkanolamine solution comprising the steps of:
(a) providing a fresh aqueous alkanolamine solution having alkanolamine concentration sufficient to effectively sorb an acid gas selected from the group consisting of $H_2S$, $CO_2$, or both from a gaseous hydrocarbon stream having $H_2S$, $CO_2$, or both dissolved therein;
(b) contacting said fresh aqueous alkanolamine solution with said hydrocarbon gas stream of step (a) whereby said fresh aqueous alkanolamine solution is enriched in said acid gas sorbed from said gaseous hydrocarbon stream;
(c) stripping said acid gas from said enriched alkanolamine solution to produce an acid-lean alkanolamine solution;
(d) recycling said acid-lean alkanolamine solution of step (c) to said contacting step (b);
(e) sequentially repeating steps (b), (c), and (d) to evolve a spent alkanolamine solution which, in its acid-lean form, is characterized by reduced acid gas sorption capacity in comparison with said fresh aqueous alkanolamine solution;
(f) removing inorganic ions from said spent alkanolamine solution;
(g) heating said spent alkanolamine solution of step (f) at temperature of from about 220° to about 275° C. for time of from about 0.25 to about 2 hours in the absence of added catalyst;
(h) admixing said heat-treated spent alkanolamine solution of step (g) with from about 0.1 to about 20 weight percent of at least one organic base selected from the group consisting of the tetraalkylammonium hydroxides which evolves no inorganic ionic constitutent upon dissolution in said spent alkanolamine solution and heating said admixture to reflux for time sufficient to produce a rejuvenated alkanolamine solution having at least about 80% of the acid gas sorption capacity of said fresh alkanolamine solution whereby the content of inorganic ionic constituent in said rejuvenated alkanolamine solution is less than when the same process is carried out with a base which forms an inorganic ionic constituent;
(i) charging said rejuvenated alkanolamine solution to said recycling step (d).

9. The process of claim 8 wherein said inorganic ion removal step (g) produces an alkanolamine solution containing not more than about 100 ppm inorganic anions and not more than about 150 ppm inorganic cations.

10. The process of claim 8 wherein said organic base is at least one selected from the group consisting of tetramethylammonium hydroxide, tetraethylammonium hydroxide, tetrapropylammonium hydroxide, and tetrabutylammonium hydroxide.

11. The process of claim 10 wherein said organic base comprises tetrabutylammonium hydroxide.

12. The process of claim 10 wherein said refluxing of step (h) is conducted at temperature of from about 120° to about 140° C.

13. The process of claim 8 wherein said rejuvenated alkanolamine solution of step (h) is charged to said recycling step (d) in the absence of an organic base removal step.

14. The process of claim 8 wherein step (g) further comprises heating said aqueous alkanolamine solution at temperature of from about 240° to about 260° C., and step (h) further comprises admixing the alkanolamine solution with said organic base in concentration of from about 0.1 to about 20 weight percent improve the acid gas sorption capacity of the aqueous alkanolamine solution by a factor of from about 1.10 to about 1.30, whereby the content of inorganic ionic constituent in said rejuvenated alkanolamine solution is not increased and is less than with a base which forms an inorganic ionic constituent by a factor of at least about 80.

* * * * *